(12) United States Patent
Roberts et al.

(10) Patent No.: US 8,933,112 B2
(45) Date of Patent: Jan. 13, 2015

(54) TOPICAL LIQUID TO AMELIORATE PAIN AND PROMOTE HEALING OF BURN-INJURED SKIN

(71) Applicants: Lee K. Roberts, Cordova, TN (US); William L. Hickerson, Memphis, TN (US); Douglas B. Learn, Doylestown, PA (US)

(72) Inventors: Lee K. Roberts, Cordova, TN (US); William L. Hickerson, Memphis, TN (US); Douglas B. Learn, Doylestown, PA (US)

(73) Assignee: Memphaceuticals, LLC, Cordova, TN (US)

( * ) Notice: Subject to any disclaimer, the term of this patent is extended or adjusted under 35 U.S.C. 154(b) by 148 days.

(21) Appl. No.: 13/799,113

(22) Filed: Mar. 13, 2013

(65) Prior Publication Data

US 2013/0338206 A1 Dec. 19, 2013

Related U.S. Application Data

(60) Provisional application No. 61/660,423, filed on Jun. 15, 2012.

(51) Int. Cl.
*A61K 31/415* (2006.01)
*A61K 31/4174* (2006.01)
*A61K 9/00* (2006.01)
*A61K 47/10* (2006.01)

(52) U.S. Cl.
CPC ........... *A61K 31/4174* (2013.01); *A61K 9/0014* (2013.01); *A61K 47/10* (2013.01)
USPC ....................................... 514/396

(58) Field of Classification Search
CPC .......................... A61K 31/4174; A61K 9/0014
USPC ....................................... 514/396
See application file for complete search history.

(56) References Cited

U.S. PATENT DOCUMENTS

| | | | |
|---|---|---|---|
| 4,654,323 | A | 3/1987 | Beitner |
| 4,777,171 | A | 10/1988 | Beitner |
| 4,910,197 | A | 3/1990 | Beitner |
| 6,562,326 | B1 | 5/2003 | Miller |
| 7,094,431 | B2 | 8/2006 | Peshoff |
| 7,604,797 | B2 | 10/2009 | Hicks |

OTHER PUBLICATIONS

Alonso et al. Agonist-induced $Ca^{2+}$ influx into human platelets is secondary to the emptying of intracellular $Ca^{2+}$ stores. Biochem. J. vol. 280 (1991), pp. 783-789.
Alvarez et al. Cytochrome P-450 may link intracellular $Ca^{2+}$ stores with plasma membrane $Ca^{2+}$ influx. Biochem. J. vol. 274 (1991), pp. 193-197.
Alvarez et al. High affinity inhibition of $Ca^{2+}$-dependent $K^+$ channels by cytochrome P-450 inhibitors. J Biol Chem 267 vol. 267, No. 17 (1992), pp. 11789-11793.
American Burn Association. Burn Incidence and Treatment in the United States: 2012 Fact Sheet. (2012). American Burn Association, available at <http://www.ameriburn.org/resources_factsheet.php>.
Ayub and Levell. Structure-Activity Relationships of the Inhibition of Human Placental Aromatase by Imidazole Drugs Including Ketoconazole. J. Steroid. Biochem. vol. 31, No. 1 (1988), pp. 65-72.
Ballard et al. A Comparative Study of 1-Substituted Imidazole and 1,2,4-Triazole Antifungal Compounds as Inhibitors of Testosterone Hydroxylations Catalysed by Mouse Hepatic Microsomal Cytochromes P-450. Biochemical Pharmacology, vol. 37, No. 24 (1988), pp. 4643-4651.
Bruns et al. Polyethylene glycol intoxication in burn patients. Burns, vol. 9 No. 1 (1982), pp. 49-52.
Department of Health and Human Services, Food and Drug Administration. Feb. 8, 2002. 21 CFR § 333. Topical Antifungal Drug Products for Over-the-Counter Human Use; Amendment of Final Monograph. Federal Register 67(27):5942-5943.
Jensen et al. Inhibition of T cell proliferation by selective block of $Ca^{2+}$-activated $K^+$ channels. Proc. Natl. Acad. Sci. USA, vol. 96 (1999), pp. 10917-10921.
Khanna et al. hSK4/hIK1, a Calmodulin-binding $K_{Ca}$ Channel in Human T Lymphocytes: Roles in proliferation and volume regulation. J. Biol. Chem. vol. 274 (1999), pp. 14838-14849.
Mason et al. Imidazole Antimycotics: Inhibitors of Steroid Aromatase. Biochemical Pharmacology, vol. 34, No. 7 (1985), pp. 1087-1092.
Mayo Clinic. Causes. Mayo Foundation for Medical Education and Research. (Aug. 21, 2012), http://www.mayoclinic.com/health/burns/DS01176/DSECTION=causes>.
Mayo Clinic. Burns: First Aid. Mayo Foundation for Medical Education and Research, (Feb. 1, 2012), http://wvvw.mayoclinic.com/health/first-aid-burns/FA00022.
Montero et al. Agonist-induced $Ca^{2+}$ influx in human neutrophils is secondary to the emptying of intracellular calcium stores. Biochem. J. vol. 277 (1991), pp. 73-79.
Papp et al. The progression of burn depth in experimental burns: a histological and methodological study. Burns, vol. 30 (2004), pp. 684-690.
Penso and Beitner. Clotrimazole decreases glycolysis and the viability of lung carcinoma and colon adenocarcinoma cells. European Journal of Pharmacology, vol. 451 (2002), pp. 227-235.

(Continued)

*Primary Examiner* — Renee Claytor
(74) *Attorney, Agent, or Firm* — Thompson Hine LLP

(57) ABSTRACT

A novel method and composition is disclosed for treating burn injuries on human skin by promoting healing of the damaged skin. In particular, a topical liquid drug formulation is used to treat burn injuries caused by exposure of the skin to heat (thermal burns), the sun or ultraviolet radiation (sunburn), ionizing radiation (radiation burns), chemicals (chemical burns) and electricity (electrical burns). The topical burn treatment liquid contains clotrimazole as the active pharmaceutical ingredient to promote the healing of the burn damaged skin by reducing the edema, erythema, blistering, pain and other symptoms associated with burns, as well as preventing the spread of the burn damage and promoting healing.

18 Claims, 1 Drawing Sheet
(1 of 1 Drawing Sheet(s) Filed in Color)

(56) References Cited

OTHER PUBLICATIONS

Rodrigues et al. Interactions of Imidazole Antifungal Agents with Purified Cytochrome P-450 Proteins. Biochemical Pharmacology, vol. 36, No. 24 (1987), pp. 4277-4281.

Sheets et al. Inhibition of Rat Liver Microsomal Cytochrome P-450 Steroid Hydroxylase Reaction by Imidazole Antimycotic Agents. Biochemical Pharmacology vo. 35, No. 3 (1986), pp. 487-491.

Singer et al. Standardized Burn Model Using a Multiparametric Histologic Analysis of Burn Depth. Academic Emergency Medicine, vol. 7, No. 1 (2000), pp. 1-6.

Singer et al. Validation of a porcine comb burn model. American Journal of Emergency Medicine, vol. 27 (2009), pp. 285-288.

Spiekermann et al. Clinical Evaluation of Clotrimazole: A Broad-Spectrum Antifungal Agent. Arch Dermatol, vol. 112 (1976), pp. 350-352.

The Burn Resource Center, Medical Care Guide, Burn Statistics, (2011), available at www.burnsurvivor.com/burn_statistics.html.

University of Maryland Medical Center. Burns (1997-2013), http://www.umm.edu/altmed/articles/burns-000021.htm.

Van den Bossche et al. Hypothesis on the molecular basis of antifungal activity of N-substituted imidazoles and triazoles. Biochem Soc. 604th Meeting, Cambridge, vol. 11 (1983), pp. 665-667.

Wolff et al. The Dual Mode of Inhibition of Calmodulin-Dependent Nitric-Oxide Synthase by Antifungal Imidazole Agents. J Biol Chem. vol. 268, No. 13 (1993), pp. 9430-9436.

Yoshida and Aoyama. Interaction of Azole Antifungal Agents with Cytochrome $P-450_{14DM}$ Purified from *Saccharomyces cerevisiae* Microsomes. Biochemical Pharmacology, vol. 36, No. 2 (1987), pp. 229-235.

Zancan et al. Clotrimazole inhibits and modulates heterologous association of key glycolytic enzyme 6-phosphofructo-1-kinase. Biochemical Pharmacology, vol. 73 (2007), pp. 1520-1537.

TOPICAL LIQUID TO AMELIORATE PAIN AND PROMOTE HEALING OF BURN-INJURED SKIN

This application claims priority from U.S. Application Ser. No. 61/660,423 filed Jun. 15, 2012, which is expressly incorporated by reference herein in its entirety.

The invention relates to the novel use of clotrimazole as the only active component in a method topically applying liquid clotrimazole to burn-injured human skin under conditions and in a formulation that promoted healing and reduced pain in treating burn-injured skin.

A burn injury to the skin can be caused by exposure to excessive heat. For example, exposure to fire, boiling water, steam, hot metal objects (e.g., cooking pans, oven grills) etc. can cause thermal burn injury to human skin (Mayo Clinic, 2010). It is also well documented that burn injuries to human skin can be caused by exposure to the sun, ultraviolet (UV) radiation, abnormal cold, chemicals, poison gas, electricity, or ionizing radiation (Mayo Clinic, 2010).

Burns to the skin are characterized by a painful reddening and swelling of the epidermis (first-degree); damage of the tissue extending to the dermis, usually with blistering, scabbing, and in some cases scarring (second-degree); destruction of the epidermis and dermis extending into the deeper tissue with a loss of pain receptors (third-degree); or, in extreme cases, damage extending to the muscle tissue beneath the skin (fourth-degree) with the potential for infections and auxiliary damage to internal organs (University of Maryland Medical Center, 2011). While first and second degree burns, and to some extent third-degree burns over a small area, are self-resolving; severe and extensive third and fourth degree burns require clinical intervention and often hospitalization.

Even relatively minor burns are painful, cause discomfort, become infected, and/or depending on the depth of the injury, lead to scabbing and scarring during a prolonged healing process.

About 2.4 million burn injuries are reported in the United States each year (Burn Survivor Center, 2001). The Centers for Disease Control and Prevention estimates that there are between 30-35 million total burn injuries annually (personal communication). Nearly 450,000 of these burn injuries are treated by medical professionals, with 45,000 requiring the patient to be hospitalized and 3,500 ending in death (American Burn Association, 2011).

Current treatments for burn injuries vary by the degree of the injury. They include pain relief agents, herbal and/or tertiary topical ointments, dressings, and devices. For minor burn injuries, defined as first (superficial) and second (partial thickness) degree thermal burns covering less than 10% of total body surface area (TBSA), and third (full thickness) degree burns covering less than 2% TBSA, the Mayo Clinic (Mayo Clinic, 2012) suggests cooling the burn under running water, covering the injury with a sterile gauze bandage, and taking an over-the-counter (OTC) pain reliever. More serious burns, those that may impair blood flow and lead to stasis and the eventual necrosis of cells in and around the injury, are treated in the clinical setting with wound dressings that are moistened to aid in healing, topical antimicrobial agents to limit and prevent infection, hydration, elevation to reduce swelling, and management of systemic diseases.

While severe burns require medical care, most minor burns are self-resolving (University of Maryland Medical Center, 2011). First-degree burn injuries generally heal in 3 to 6 days with the superficial skin occasionally peeling off in 1 to 2 days. The healing time of second-degree burns varies depending on the severity of the burn, but can take 3 weeks or more. The healing time for third-degree burns varies even more widely, with full-thickness burns often requiring skin grafts and other radical treatments.

Beitner U.S. Pat. Nos. 4,654,323; 4,777,171; and 4,910,197 describes protein kinase C (PKC) inhibitors and calmodulin inhibitors having the "ability to interfere with the action of the calcium calmodulin complex in vivo in the mammalian body" which are able to "promote healing of skin tissue and aid in preventing or alleviating the damaging effects of trauma on the skin of the mammalian body." U.S. Pat. No. 4,654,323 teaches a method and compositions for the therapeutic and prophylactic treatment of skin trauma, in particular burns, sunburn, and frostbite. Beitner's burn treatment compounds, having the ability to interfere with the action of the calcium calmodulin complex, include phenothiazines, thioxanthenes, butyrophenones, diphenyl-butylamines, dibenzodiazepines, benzodiazepines, dibenzazepines, and naphthalenesulfonamides. Beitner's claimed pharmaceutical composition is comprised of an ointment, cream, or lotion that contains from 4% to 40% by weight of a compound that has the ability to interfere with the action of the calcium calmodulin complex. In further claims, as well as in U.S. Pat. No. 4,777,171, the composition is described as containing trifluoperazine as the compound for interfering with the action of the calcium calmodulin complex, and the addition of an effective amount of a local anesthetic and any anti-infective agent selected from neomycin, bacitracin, silver sulfadiazine, gentamicin, polymyxin, and mafenide acetate. U.S. Pat. No. 4,910,197 claims a composition comprising an ointment, cream, or lotion which contains 4% to 40% by weight of trifluoperazine. Based on these patents the effective pharmaceutical concentration of a calmodulin inhibitor for treating a burn injury to the skin must be equal to or greater than 4% by weight of the composition.

Clotrimazole was developed as an antifungal agent (Spiekermann and Young, 1976) and is approved for that use in the United States by the U.S. Food and Drug Administration (Department of Health and Human Services, 2002). As such, several U.S. Patents, e.g., U.S. Pat. Nos. 7,604,797; 7,094,431; and 6,562,326) have included clotrimazole in their disclosed burn treatment formulations to prevent fungal infections to the burn injured skin. These patents teach that clotrimazole is used in burn treatment formulations and under conditions that provide only an antifungal effect, i.e., at a concentration of at least 1% w/v and without isopropyl alcohol and without polyethylene glycol. None describe clotrimazole as providing anything other than an antifungal effect. None describe the inventive compositions and uses of a non-aqueous composition of propylene glycol (CAS No. 57-55-6. the same chemical entity as 1,2-propanediol), either with or without isopropyl alcohol, i.e., isopropyl alcohol is optional, with clotrimazole. These patents do not indicate that it has any effect or activity for treating the burn injury or damage to the skin caused by the burn. For example, a composition in U.S. Pat. No. 7,604,797 contains therapeutically effective amounts of sodium monofluorophosphate (1.5% to 15% w/v), a dihydrofolate reductase inhibitor (0.001 to 100 mg/70 kg body weight), and a pharmaceutically acceptable carrier. The pharmaceutically acceptable carrier comprises dicalcium phosphate dehydrate (about 21.4% by weight), insoluble sodium metaphosphate (about 13% by weight), sorbitol syrup solution (about 23.3% by weight), guar gum (about 4.2% by weight), xanthan gum (about 1.7% by weight), monosodium phosphate (about 0.28% by weight), titanium dioxide (about 0.56% by weight), sodium dodecylbenzene sulphate (about 0.46% by weight), water (about 22.4% by weight), trimagnesium phosphate (about 0.74% by weight), and hydroxyethyl cellulose ester (about 2.9% by weight). The pharmaceutical composition contains one or more of the following antifungal agents: terbinafine hydrochloride, nystatin, amphotericin B, griseofulvin, ketoconazole, miconazole nitrate, flucytosine, fluconazole, itraconazole, clotrimazole, benzoic acid, salicylic acid, voriconazole, caspofungin, and selenium sulfide. There is no indication of what concentration of antifungal agent is to be used in preparing the composition. In U.S. Pat. No. 7,094,431 a therapeutic tissue healing composition is described comprised of an effective amount of a mixture of zinc oxide (between about 0.01% and 75% by total weight), fat-soluble vitamins A, D, E, K (between about 0.01% and 99.99% by total weight), an effective amount of an antibacterial agent, an effective amount of an antifungal agent, and an effective amount of calcium channel blocker listed as 3,5-pyridinedicarboxylic acid, 1,4-dihydro-2,6-dimethyl-4-(2-nitrophenyl)-dimethyl ester, which has the chemical formula of $C_{17}H_{18}N_2O_6$ specified as nifedipine between 0.0001% and 50% by total weight. The antifungal agents listed are astemizole, clotrimazole, omeprazole, econazole, oxiconazole, sulconazole, fluconazole, ketoconazole, itraconazole, terfinafine, and mixtures thereof. There is no indication of the concentration to prepare the therapeutic composition. In U.S. Pat. No. 6,562,326 a method for treating burns comprises topical administration of a composition consisting of a combination of tetracaine (about 1% to 2% by weight) and sodium lauryl sulfate (about 0.5% to 5% by weight) in a pharmaceutically acceptable carrier. An embodiment suggests that the composition can also contain antimicrobials, including antibiotics, antifungals and other anti-viral compounds which may complement or supplement the activity of the basic composition. The examples of antifungals listed in the patent were tolnaftate and micatin with no indication of the amount to be used in the composition.

The reported antifungal mechanism of action of imidazole compounds, such as clotrimazole, is due to their inhibition of sterol 14α-demethylase, a microsomal cytochrome P-450-dependent enzyme (Vanden Bossche et al. 1983; Yoshida and Aoyama, 1987). Imidazole antimycotics are also shown to be potent inhibitors of many mammalian cytochrome P-450-mediated reactions (Ayub and Levell 1988; Ballard et al. 1988; Mason et al., 1985; Rodrigues et al.; 1987; Sheets et al.; 1986). Alvarez et al. (1991) reported that imidazole antimycotics are potent inhibitors of rat thymocyte plasma membrane $Ca^{2+}$ channels that are activated by emptying the intracellular $Ca^{2+}$ stores. The same mechanism of $Ca^{2+}$ channel inhibition by imidazole antimycotics has been reported for human neutrophils (Montero et al. 1991) and platelets (Alonso et al., 1991). Alvarez et al. (1992) reported that among several imidozole antimycotics, i.e., tioconazole, miconazole and econazole, clotrimazole was the most potent inhibitor of $Ca^{2+}$-dependent $K^+$ channels of human red blood cells, rat thymocytes, and Ehrlich ascites tumor cells. Wolff et al. (1993) reported that clotrimazole inhibited citrulline formation by nitric-oxide synthase in bovine brain. Clotrimazole also inhibited the cytochrome-c reductase activity of nitric-oxide synthase and cyclic-nucleotide phosphodiesterase in a calmodulin-dependent fashion. Wolff et al. (1993) concluded that their observations were consistent with a mechanism whereby antifungal imidazoles inhibit citrulline formation by interaction with the nitric-oxide synthase at two points. That is, imidazoles may act as calmodulin antagonists to reduce the responsiveness of the enzyme to activation by calmodulin, or by their putative binding to heme iron, reducing the maximal velocity of citrulline formation.

Numerous reports now indicate the calmodulin inhibiting activity of clotrimazole. For example, Khanna et al. (1999) examined a $Ca^{2+}$-activated $K^+$ channel in human T lymphocytes. The authors showed that this channel had a $Ca^{2+}$-dependent calmodulin-binding site proximal to its C terminus that could be inhibited by calmodulin antagonists such as clotrimazole. Jensen et al. (1999) showed that clotrimazole inhibits activation of human T lymphocytes by blocking $Ca^{2+}$-sensitive $K^+$ channels. It was suggested that calmodulin antagonists, like clotrimazole, could be used as effective immune suppressive drugs. While imidazoles have been shown to act as calmodulin antagonists in a variety of cell types, to our knowledge none of these studies have been conducted in human skin. More recently, calmodulin antagonists, including clotrimazole, have been shown to have anti-cancer treatment properties through their ability to inhibit the activity of various glycolytic enzymes. Zancan et al. (2007) showed that clotrimazole directly inhibits the glycolytic enzyme 6-phosphofructo-1-kinase (PFK), which was independent of its anti-calmodulin activity. Clotrimazole caused dimerization of PFK, the dimers are less active than the normal tetramer form of the enzyme. The authors conclude that their data demonstrate an unrecognized action of clotrimazole as a negative modulator of glycolytic flux through direct inhibition of the key enzyme PFK. Similarly, Penso and Beitner (2002) reported that clotrimazole caused a significant reduction in the levels of two glycolytic enzymes glucose 1,6-bisphosphate and fructose 1,6-bisphosphate, ATP, and cell viability of Lewis lung carcinoma cells and CT-26 colon adenocarcinoma cells. Collectively, these studies indicate that clotrimazole may have numerous pharmacological activities based on the different mechanisms of action attributed to this drug and thus various therapeutic applications. Therefore, these studies neither provide a direct link nor describe a composition containing clotrimazole that would be suitable or specifically designed for treating thermal burn injuries on human skin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
FIG. 1 is a photograph of a mixed first and second degree thermal burn immediately following an initial application of the inventive therapy.

As used herein, weight per weight percent is indicated by w/w, volume per volume percent is indicated by v/v, and weight per volume percent is indicated by w/v.

The inventive method treated burn-injured human skin in a patient in need of this treatment using a composition comprising clotrimazole as the only active agent. Clotrimazole (1-(o-chloro-α,α-diphenylbenzyl)imidazole [CAS Number 23593-75-1]), has the following chemical structure

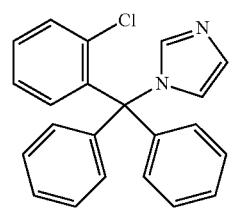 [SMILES: Clc1ccccc1C(c1ccccc1)(c1ccccc1)n1ccnc1]

a chemical formula of $C_{22}H_{17}ClN_2$, and a molecular weight of 344.84. USP grade clotrimazole contains not less than 98.0 percent and not more than 102.0 percent of $C_{22}H_{17}ClN_2$, calculated on the dried basis. In one embodiment, the composition comprises clotrimazole as the active ingredient along with a formula vehicle. In one embodiment, the formulation vehicle is propylene glycol only, with no other excipient or vehicle. Propylene glycol is typically used to stabilize formulations, it is not typically used in the art as the sole excipient or vehicle for an active. It the inventive method, propylene glycol retains the active, clotrimazole, at the site of application, thus facilitating or enhancing clotrimazole penetration into burn-injured skin. In one embodiment, the formula vehicle is a C2 or C3 alcohol (ethyl alcohol or ethanol, propyl alcohol, isopropanol, isopropyl alcohol) and propylene glycol. In embodiments with isopropanol, which is optional, isopropanol facilitates clotrimazole solubility, but clotrimazole also was solubilized without isopropanol. In one embodiment, the formula vehicle is prepared by mixing ethyl alcohol with propylene glycol at 5:1 (v/v). In one embodiment, the formula vehicle is prepared by mixing isopropyl alcohol with propylene glycol at 1:4 (v/v). In one embodiment, the C2- or C3 alcohol:propylene glycol of the formula vehicle ranges from 0:1 to 5:1, i.e., it ranges from no C2- or -C3 alcohol fraction to 83%:17%. In one embodiment, clotrimazole is present in the composition at 0.5% (w/v). In one embodiment, the formulation applied to a patient is non-aqueous. The suitable range of concentration of clotrimazole in the composition is 0.25% (w/v) to 1% (w/v) inclusive. In one embodiment, the 0.5% (w/v) clotrimazole liquid composition is prepared by dissolving 0.5 grams of clotrimazole in 100 mL of the formula vehicle. In one embodiment, the composition further comprises additional excipients or ingredients, e.g., polyacrylic acid, Carbopols®, polyvinyl pyrrolidone, acrylates, acrylamides, and/or copolymers, provided to the formulation to create a gel, film-former, mist or other effective pharmaceutical formulation acceptable for effective treatment of a burned skin.

In one embodiment, the described composition is provided in a bottle, such as a low-density polyethylene bottle, and fitted with a dropper tip or a continuous spray pump. In one embodiment, the composition is packaged in and dispensed from a medical-grade aerosol can.

In one embodiment, the described composition is applied to the area of the skin affected by a thermal burn, e.g., by dropper or spray pump. In one embodiment, a method for ameliorating at least one consequence of a burn injury to human skin is provided, the method comprising topically applying a liquid composition to an effected area of the burn injury, the composition comprising an effective amount of clotrimazole as the only active ingredient, and ameliorating at least one consequence of a burn injury which can include, but is not limited to, full-thickness necrosis, erythema, edema, and/or eschar formation. In one embodiment, the burn injury is a thermal burn, and is categorized as a first, a second, or a third degree burn.

In one embodiment of the method, the concentration of clotrimazole in the liquid composition is between 0.25% weight/volume and 1% weight/volume of the liquid composition. In one embodiment of the method, the concentration of clotrimazole in the liquid composition is 0.5% weight/volume of the liquid composition. In one embodiment of the method, the composition further comprising at least one component selected from the group consisting of ethyl alcohol, isopropyl alcohol, n-propyl alcohol propylene glycol, polyethylene glycol, water, and combinations thereof. In embodiments, the liquid composition is topically applied either directly to the affected area of the burn injury by pouring, applying by a dropper, or spray dispensed from a primary drug container fitted with an appropriate dispensing cap or device, or the liquid composition is applied to a sterile gauze pad or other dressing that is used to cover the affected area of the burn injury. In one embodiment, the liquid composition is applied to cover the entire affected area of the burn injury area. In one embodiment, the liquid composition is applied within three hours of the burn exposure.

In embodiments, the method further comprises repeating the topical application of the liquid composition to the affected area of the burn injury daily until the burn injury is healed. In one embodiment, the method further comprises topically applying the liquid composition to the affected area of the burn injury from 1 to 4 times daily. In one embodiment, the liquid composition is a viscous liquid that air-dries on the site of application.

In various embodiments, the burn injury is a result of exposure to at least one of fire, boiling water, steam, hot metal objects, hot liquids of any type, hot materials of any type, sun, ultraviolet radiation, abnormal cold, chemicals, poison gas, electricity, and/or ionizing radiation.

The following examples are intended to illustrate the utility of the present invention but are not intended to and do not limit the claim scope.

Commercial Preparations.

Clotrimazole is an active antifungal ingredient that is marketed for the treatment of athlete's foot (tinea pedis), jock itch (tinea cruris), ringworm, and oral thrush (oropharyngeal candidiasis). As a topical antifungal, clotrimazole is effective in controlling infections caused by fungi such as *Tricophyton rubrum, T. mentagrophytes* and *Epidermaphyton floccosum*. Effective antifungal pharmaceutical preparations for treatment of dermal fungal infections must be formulated at clotrimazole concentrations of at least 1%. In some examples below, commercially available antifungal products, e.g., Lotrimin®, formulated as 1% clotrimazole in polyethylene glycol, were used for proof of concept only. That is, based on the disclosure herein of the 0.5% clotrimazole liquid, these formulations were not suitable for the disclosed method of treatment. For example, the concentration of clotrimazole, 1%, when formulated in a cream or topical spray powder, was not as effective for treating burns as a concentration less than 1% formulated in a liquid. Further, the use of polyethylene glycol as the only solvent in the formula vehicle (e.g., Lotrimin®) may not be safe for treating burns (Bruns et al. 1982), especially burns that cover a large body surface. Bruns reported three burn patents died of acute renal failure following treatment with a polyethylene glycol based burn cream. All three patients had ethylene glycol in their circulation and were acidotic with increased anion and osmolal gaps. This syndrome was similar to that of common poisoning with ethylene glycol but also included an increase serum calcium with a concomitant decrease in ionized calcium. The cause of this high "calcium gap" appeared to be binding of calcium by dicarboxylic acid metabolites of polyethylene glycol.

Experimental Animal Models.

Validated and/or standardized non-human burn models exist that can be used to show progression of induced thermal burned skin into full-thickness necrosis (Singer et al. 2009) the consistency of burn depth (Singer et al. 2000) and the histology of burn injuries (Papp et al. 2004). Porcine burn models can show how contact times create burns of different depths (Papp et al. 2004; Singer et al. 2000) and how burn injuries progress and affect non-burned skin (Singer et al. 2009). Burn models have been established at various temperatures, contact times with burn agents, and pressure applied by the burn agent. Such porcine models and anecdotal human experience have been used to show utility of the inventive method using clotrimazole liquid.

Preparation of Clotrimazole Liquid.

Raw materials, i.e., clotrimazole, isopropyl alcohol if used, and propylene glycol, were procured from a commercial chemical supply company and blended in a research laboratory.

Preparation of Clotrimazole Formulations:

Formulation A: isopropyl alcohol with propylene glycol at 1:4 (volume/volume) as the formula vehicle for clotrimazole. Isopropyl alcohol was mixed with propylene glycol at 1:4 (v/v) as the vehicle for clotrimazole. The 0.5% w/v clotrimazole liquid was prepared by dissolving 0.5 g clotrimazole in 100 mL of the isopropyl alcohol/propylene glycol vehicle.

Formulation B: 0.5% clotrimazole (w/v) in propylene glycol as the only excipient in the formulation vehicle. Five gram clotrimazole was weighed and placed into a 1 L volumetric flask. About 900 mL propylene glycol was added, a stir bar was placed in the flask, and the solution was mixed on a combination heating plate/magnetic stirring device until clotrimazole was dissolved. The temperature of the heating plate did not exceed 40° C. Propylene glycol was added to q.s. to 1000 mL and mixed. After thorough mixing, the stir bar was removed, the solution was placed in a desired container and the container was capped tightly. The solution was 0.5% (w/v) clotrimazole in propylene glycol.

Formulation C: 0.5% clotrimazole (w/v) in 75% ethanol, 15% 1,2-propanediol, and 10% water. Five grams clotrimazole was weighed and placed in a 1 L volumetric flask. About 700 mL ethanol was added, a stir bar was placed in the flask, and the solution was mixed on a magnetic stirring device until clotrimazole was dissolved. Ethanol was then added to q.s. to 750 mL. One hundred fifty (150) mL was added to the flask and mixed into the clotrimazole/ethanol solution, then 100 mL water was added and mixed. After thorough mixing, the stir bar was removed, the solution was placed in a desired container and the container was capped tightly. The solution was 0.5% clotrimazole in a 15:3:2 ethyl alcohol:propylene glycol:water formula vehicle.

Other formulas may be used as described below. Any formulation may be packaged in a desired suitable container, e.g., a low-density or high-density polyethylene bottle, bottle fitted with a dropper tip, bottle fitted with a continuous spray pump, etc. as known in the art. One skilled in the art appreciates that other pharmaceutical ingredients could be added to the formulation to create a gel, film-former, mist, etc. or other effective pharmaceutical formulation acceptable for effective treatment of a burned skin. It is also possible that the acceptable pharmaceutical formulation could be packaged in and dispensed from a medical-grade aerosol can.

EXAMPLE 1

Clotrimazole Formulation A is used employing a burn injury model in pigs. A brass comb creates four burns interspaced by unburned skin (Singer et al. 2009). To induce burns on the pig's skin, the brass comb is pre-heated in boiling water and applied to the animals' dorsum for 30 seconds, which results in four rectangular 10×20 mm full-thickness burns separated by 5×20 mm unburned interspaces. Following the induction of the burn injuries, different burn sites are treated with a clotrimazole liquid or left untreated.

During a seven day observation period, 97.7% of the burn injuries that were left untreated spread to the unburned tissue and progress to full-thickness necrosis. In contrast, burn sites treated by applying a clotrimazole liquid directly to the burn injured skin do not progress to full-thickness necrosis and are resolved within the 7 day observation period. In this example, a commercial antifungal liquid consisting of 1% (w/v) clotrimazole dissolved in polyethylene glycol 400 is assessed as a proof of concept for treating a thermal burn. The clotrimazole liquid is applied from a dropper bottle in an amount to completely cover the burn injured skin once per day over the course of the experiment.

EXAMPLE 2

An experiment is conducted as described in Example 1. During a seven day observation period, 100% of the burn injuries that were left untreated show significant signs of erythema, edema and eschar formation. These conditions do not resolve during the seven day observation period. In contrast, burn sites treated by applying a clotrimazole liquid directly to the burn injured skin halt the progression of erythema and edema, and promote re-epithelialization leading to reduced eschar formation and faster healing within the seven day observation period. In this example, the liquid formulation consists of 0.5% (w/v) clotrimazole dissolved in a solution of 20% isopropyl alcohol and 80% propylene glycol. The 0.5% clotrimazole liquid is delivered from a plastic bottle fitted with a dripper cap or spray pump in an amount to completely cover the burn injured skin once per day over the course of the experiment.

EXAMPLE 3

An experiment was conducted as described in Example 1. During a seven day observation period, nearly 100% of the burn injuries that were left untreated showed significant signs of erythema, edema and eschar formation. These conditions do not resolve during the seven day observation period. Compared to the experimental 0.5% clotrimazole liquid, treating the burn sites with a non-liquid formulation of 1% clotrimazole, e.g., Lotrimin AF® Jock Itch Antifungal Cream or Canesten® Cream, available over the counter (OTC), does not lead to faster healing of the burn injury. The edema and erythema on the burn injury sites treated with the non-liquid formulation of 1% clotrimazole do not resolve within the seven day observation period. Thus, unlike the effectiveness of the 0.5% clotrimazole liquid for treating burns, application of alternative, non-liquid 1% clotrimazole formulations do not lead to healing of burn injuries.

EXAMPLE 4

The index and middle fingers on the hand of an adult woman were exposed to steam from a boiling tea pot. The resulting thermal burn, if left untreated, would cause injury to the micro vessels perfusing the area, resulting in the leakage of large amounts of plasma. The plasma leakage, in turn, would lift off the heat-destroyed epidermis, causing blister formation. The blisters would continue to increase in size in the post-burn period as well as protein breakdown occurring. A light pink, wet-appearing and very painful wound is seen as blisters are disrupted. Frequently, the epidermis does not lift off the dermis for 12 to 24 hours and what appears initially to be a first degree burn is actually a second degree burn. Such a thermal burn would take 1-2 weeks to resolve.

In this case, the woman with the steam burn injury is treated with a solution of 0.5% (w/v) clotrimazole dissolved in propylene glycol. This clotrimazole liquid is first applied within five minutes of exposure to the steam. The affected areas are liberally covered with the clotrimazole liquid which is reapplied on each of the following two days. Upon application of the first clotrimazole treatment, the pain associated with the burn is resolved. Within 24 hours, the erythema and edema are greatly reduced and the burn injured skin is healed in approximately four days without blistering, scabbing, or scarring.

EXAMPLE 5

The dorsal surface of the hand of an adult male who accidentally touched hot oven racks at an approximate temperature of 250° F. was analyzed. The resulting thermal burn, if left untreated, would cause a mix of edema and erythema specifically on skin that got close to but did not actually touch the oven rack, and injury of the micro vessels perfusing the area, resulting in the leakage of large amounts of plasma, which in turn lifts off the heat-destroyed epidermis causing blister formation as described in Example 4. Additionally, injured areas that touched the oven rack for the longest periods of time would result in small patches of dry, leathery skin that is black, white, brown, or yellow with swelling and a lack of pain because the nerve endings have been destroyed. These areas would heal poorly and slowly without medical attention, while the lesser burned areas would take 2-6 weeks to resolve.

In this case, the man with the oven rack burn injury is treated with 0.5% (w/v) clotrimazole dissolved in a solution of propylene glycol. This 0.5% clotrimazole liquid is first applied within 20 minutes of contact with the oven rack. The affected areas are liberally covered with the clotrimazole liquid, which is reapplied once daily on the following eight days. Upon application of the first clotrimazole treatment, the pain associated with the burn is resolved. Within 24 hours, the erythema and edema are greatly reduced and the burn injured skin is healed in approximately eight days without blistering or scabbing (eschar).

EXAMPLE 6

When a severely burned patient, who was a victim of a home fire, was admitted to the hospital, the attending burn treatment physician applies a commercial 1% clotrimazole liquid to the injured areas of the face. In this example, the treated injuries on the face are first and second degree burns. The Lotrimin® like clotrimazole liquid formula used to treat these injuries is comprised of 1% (w/v) clotrimazole dissolved in polyethylene glycol 400. The 1% clotrimazole liquid is applied to the burn injuries on the face twice per day using a dropper bottle. The administration of the 1% clotrimazole liquid is continued until the burn injuries are healed. Through clinical practice, with this and other patients, it is observed that application of the 1% clotrimazole liquid reduces the spread of the damage and speeds healing of the burn damaged skin, often by promoting eschar formation, resulting in a better cosmetic outcome for the patient.

EXAMPLE 7

A sunburn on human skin causes pain, irritation and redness. These burns can lead to the peeling of the surface layer of skin, as well as blistering and scarring. When sunburn is treated with a solution of 0.5% clotrimazole in 20% isopropyl alcohol and 80% propylene glycol, it is less painful and heals faster than if left untreated. Depending on the severity of the sunburn, areas treated with the 0.5% clotrimazole liquid are less likely to peel and blister.

EXAMPLE 8

Two-hundred and forty patients with severe thermal burn injuries, including extensive first and second degree burns to the face, are admitted to a regional burn center over a three year period. The 240 patients are treated by a physician with a Lotrimin® like solution: 1% (w/v) clotrimazole dissolved in polyethylene glycol 400. The Lotrimin® like solution is applied topically to the burned skin one to four times daily. The treatment is well tolerated. The treatment helps to resolve the burn injury to the face by promoting eschar formation, which limits the spread of damage and sped the healing process. The patients receiving this treatment have a cosmetic outcome.

EXAMPLE 9

A 63 year old male, Fitzpatrick Skin Type III, received a first degree thermal burn to the left buttock and upper thigh with areas of second degree thermal burn on the upper thigh. The thermal burn was caused by sitting for 45-60 minutes on a hot, dark-colored asphalt shingle roof during maintenance work. The injury occurred between 2:30-3:30 pm in late September in Memphis Tenn., on a day with a clear sky and an ambient air temperature of about 88° F. The individual was wearing denim jeans throughout the time of the exposure.

The thermal burned skin was marked by erythema, was painful to touch, and some areas included papules and weeping. At about 4:30 pm (approximately one hour post-exposure and after a shower, the entire area was treated with Formula B above: a liquid solution of 0.5% clotrimazole (w/v) dissolved in propylene glycol. The condition of the area immediately following treatment with a topical application of the treatment solution is shown in FIG. 1. The treatment solution was dispensed from a dropper bottle, liberally applied to the burned skin area, and lightly spread over the area with a finger.

Figure 2:
FIG. 2 is a photograph of the same thermal burn of FIG. 1 about 15.5 hours after the initial therapy application.

Immediately following application pain was greatly reduced. The next day, about 15.5 hours after this single treatment with the topically applied 0.5% clotrimazole liquid, the burned skin area was observed to be nearly completely healed, shown in FIG. 2. That is, the erythema and pain were completely resolved. Except for some slight discoloration the papules and weeping observed on skin areas of second degree burn were resolved.

Each of the following references, as well as those previously disclosed, is incorporated by reference herein in its entirety:

Beitner, Rivka; "Method and Composition for the Therapeutic and Prophylactic Treatment of Trauma to the Skin", U.S. Pat. No. 4,654,323, Issued Mar. 31, 1987.

Beitner, Rivka; "Method and Composition for the Therapeutic and Prophylactic Treatment of Trauma to the Skin", U.S. Pat. No. 4,777,171, Issued Oct. 11, 1988.

Beitner, Rivka; "Method and Composition for the Therapeutic and Prophylactic Treatment of Trauma to the Skin", U.S. Pat. No. 4,910,197, Issued Mar. 20, 1990.

Hicks, Terry Lee; "Compositions and Methods for Treating Burns", U.S. Pat. No. 7,604,797, Issued Oct. 20, 2009

Miller, Bruce W.; "Topical Composition for Burn Healing", U.S. Pat. No. 6,562,326, Issued May 13, 2003

Peshoff, Mickey L.; "Method of Healing Skin Wounds in Mammals and a Composition Thereof", U.S. Pat. No. 7,094,431, Issued Aug. 22, 2006

Alonso, M T, J Alvarez, M Montero, A Sanchez, J Garcia-Sancho. 1991. Agonist-induced Ca2+ influx into human platelets is secondary to the emptying of intracellular Ca2+ stores. Biochem. J. 280:783-789.

Alvarez, J, M Montero, J Garcia-Sancho. 1991. Cytochrome P-450 may link intracellular Ca2+ stores with plasma membrane Ca2+ influx. *Biochem. J.* 274:193-197.

Alvarez, J., M Montero, J Garcia-Sancho. 1992. High affinity inhibition of Ca2+-dependent K+ channels by cytochrome P-450 inhibitors. J Biol Chem 267(17):11789-11793.

American Burn Association. 2011. *American Burn Association*. <http://www.ameriburn.org/resources_factsheet.php>. Webpage accessed 24 Feb. 2012.

Ayub, M and J. Levell. 1988. Structure-activity relationships of the inhibition of human placental aromatase by imidazole drugs including ketoconazole. J. Steroid Biochem. 31:65-72.

Ballard, S A, A Lodola, M H Tarbit. 1988. A comparative study of 1-substituted imidazole and 1,2,4-triazole antifungal compounds as inhibitors of testosterone hydroxylations catalysed by mouse hepatic microsomal cytochromes P-450. *Biochem. Pharmacol.* 37:4643-4651.

Bruns D E, D A Herold, G T Rodeheaver, R F Edlich. 1982. Polyethylene glycol intoxication in burn patients. Burns Incl Therm Inj. 9(1): 49-52.

Burn Survivor Resource Center (Webpage). 2001. *Medical Care Guide—Burn Statistics* (reference to Journal of Burn Care & Rehabilitation, May/June 1992). <www.burnsurvivor.com/burn_statistics.html>. Webpage accessed 24 Feb. 2012.

Department of Health and Human Services, Food and Drug Administration. Feb. 8, 2002. 21 CFR Part 333 [Docket No. 99N-4063]. Topical Antifungal Drug Products for Over-the-Counter Human Use; Amendment of Final Monograph. Federal Register 67(27):5942-5943.

Finkelstein E A, Corso P S and Miller T R. 2006. Incidence and Economic Burden of Injuries in the United States. New York: Oxford University Press.

Jensen, B S, N Odum, N K Jorgensen, P Christophersen, S P Olesen. 1999. Inhibition of T cell proliferation by selective block of Ca2+-activated K+ channels. *Proc. Natl. Acad. Sci. USA* 96: 10917-10921.

Khanna, R, M C Chang, W J Joiner, L K Kaezmarek and L C Schlichter. 1999, hSK4/hIK1, a calmodulin-binding KCa channel in human T lymphocytes. *J. Biol. Chem.* 274: 14838-14849.

Mason, J I, B A Murry, M Olcott, J J Sheets. 1985. Imidazole antimycotics: inhibitors of steroid aromatase. *Biochem. Phurmacol.* 34:1087-1092.

Mayo Clinic (Webpage). 27 Apr. 2010. Causes. Mayo Foundation for Medical Education and Research. <http://www.mayoclinic.com/health/burns/DS01176/DSECTION=causes>. Web search on 24 Feb. 2012.

Mayo Clinic (Webpage). 1 Feb. 2012. Burns: First Aid. Mayo Foundation for Medical Education and Research. <http://www.mayoclinic.com/health/first-aid-burns/FA00022>. Web search on 24 Feb. 2012.

Montero, M, J Alvarez, J Garcia-Sancho. 1991. Agonist-induced Ca2+ influx in human neutrophils is secondary to the emptying of intracellular calcium stores. *Biochem. J.* 277: 73-79.

Papp, A, K Kiraly, M Harma, T Lahtinen, A Uusaro, E Alhava. 2004. The Progression of Burn Depth in Experimental Burns: A Histological and Methodological Study. Burns, 30:684-690.

Penso J and R Beitner. 2002. Clotrimazole decreases glycolysis and the viability of lung carcinoma and colon adenocarcinoma cells. Eur J. Pharmacol. 451(3):227-235.

Rodrigues, A D, G G Gibson, C Loannides, D V Parke. 1987. Interactions of imidazole antifungal agents with purified cytochrome P-450 proteins. *Biochem. Pharmacol.* 36:4277-4281.

Sheets, J J, J I Mason, C A Wise, R W Estabrook. 1986. Inhibition of rat liver microsomal cytochrome P-450 steroid hydroxylase reactions by imidazole antimycotic agents. *Biochem. Pharmacol.* 35:487-491.

Singer A J, L Berruti, H C Thode, S A McClain. 2000. Standardized Burn Model Using a Multiparametric Histologic Analysis of Burn Depth. Academic Emergency Medicine, 7: 1-6.

Singer A J, S A McClain, B R Taira, A Romanov, J Rooney, T Zimmerman. 2009. Validation of a porcine comb burn model. American Journal of Emergency Medicine, 27:285-288

Spiekerman P H and D Young. 1976. Clinical Evaluation of Clotrimazole: A Broad-Spectrum Antifungal Agent. Arch Dermatol. 112(3):350-352.

University of Maryland Medical Center (Webpage). 2011. Burns. <http://www.umm.edu/altmed/articles/burns-000021.htm>. Web search on 24 Feb. 2012.

Vanden Bossche H, et al. 1983. Biochem. SOC. Trans. 11:665-667.

Wolff D J, G A Datto, R A Samatovicz. 1993. The dual mode of inhibition of calmodulin-dependent nitric-oxide synthease by antifungal imidazole agents. J Biol Chem 268(13): 9430-9436.

Yoshida Y and Y Aoyama. 1987. Interaction of azole antifungal agents with cytochrome P-45014DM purified from *Saccharomyces cerevisiae* microsomes. Biochem. Pharmacol. 36:229-235.

Zancan P, A O Rosas, M C Marcondes, M M Marinho-Carvalho, M Sola-Penna. 2007. Clotrimazole inhibits and modulates heterologous association of the key glycolytic enzyme 6-phosphofructo-1-kinase. Biochem Pharmacol. 73(10):1520-1527.

Although the invention has been described in detail for the purposes of illustration, it is understood that such detail is solely for that purpose, and variations can be made therein by those skilled in the art without departing from the spirit and scope of the claimed invention.

What is claimed is:

1. A method for ameliorating at least one consequence of burn-injured mammalian skin, the method comprising topically applying to the burn-injured mammalian skin a liquid composition comprising 0.5% w/v clotrimazole as the only active ingredient to treat the burn-injured mammalian skin and at least one excipient, the composition applied to the burn-injured mammalian skin under conditions to ameliorate at least one consequence of the burn injury, the at least one consequence selected from the group consisting of partial thickness deepithelialization, full-thickness necrosis, erythema, edema, eschar formation, blistering, and/or pain.

2. A method for ameliorating at least one consequence of a burn-injured mammalian skin, the method comprising topically applying a liquid composition to an affected area of the burn-injured mammalian skin, the composition comprising clotrimazole as the only active ingredient to treat the burn-injured mammalian skin and containing at least one excipient, the concentration of clotrimazole in the composition ranging between 0.25% w/v to 1% w/v inclusive of the liquid composition, the application performed under conditions to ameliorate at least one consequence of a burn injury, the at least one consequence selected from the group consisting of partial thickness deepithelialization, full-thickness necrosis, erythema, edema, eschar formation, blistering, and/or pain.

3. The method of either claim 1 or claim 2 where the burn injury is a thermal burn, and is categorized as a first, a second, or a third degree burn.

4. The method of either claim 1 or claim 2 where the excipient is propylene glycol.

5. The method of either claim 1 or claim 2 where the at least one excipient renders the liquid composition into a gel or a film-forming liquid.

6. The method of either claim 1 or claim 2 where the at least one excipient is selected from the group consisting of propylene glycol, a two-carbon alcohol, a three-carbon alcohol, polyethylene glycol, water, buffered saline, and combinations thereof.

7. The method of claim 1 or claim 2 comprising topically applying the composition either directly or indirectly to the affected area of the burn injury.

8. The method of claim 1 or claim 2 where the liquid is applied to the affected area of the burn-injured skin by at least one of pouring, dropping, and/or spraying.

9. The method of claim 1 or claim 2 where the liquid is applied to a sterile dressing substantially covering the affected area of the burn injury.

10. The method of claim 1 or claim 2 where the liquid composition is applied to cover the entire affected area of the burn injury.

11. The method of claim 1 or claim 2 where the liquid composition is applied within three hours of the burn.

12. The method of claim 1 or claim 2 further comprising repeating the topical application of the liquid composition to the affected area of the burn injury at least daily until the burn injury is substantially healed.

13. The method of claim 1 or claim 2 further comprising repeating the topical application of the liquid composition to the affected area of the burn injury from once daily up to four times daily until the burn injury is substantially healed.

14. The method of claim 1 or claim 2 where the burn injury is a result of exposure to at least one of fire, boiling water, steam, hot metal objects, hot liquids, hot materials, sun, ultraviolet radiation, abnormal cold, chemicals, poison gas, electricity, and/or ionizing radiation.

15. The method of claim 1 or claim 2 where the liquid composition is a viscous liquid that air-dries upon application to the burn-injured skin.

16. The method of claim 1 or claim 2 where the conditions result in reduced eschar formation.

17. The method of claim 1 or claim 2 where application is direct or indirect and is by drop, spray, or mist.

18. A method for ameliorating at least one consequence of burn-injured mammalian skin, the method comprising topically applying to the burn-injured mammalian skin a composition comprising 0.5% w/v clotrimazole as the only active ingredient to treat the burn-injured mammalian skin in a formulation selected from 1:4 isopropyl alcohol:propylene glycol (v/v), propylene glycol, or 75% ethanol, 15% 1,2-propanediol, 10% water (15:3:2 ethanol:propylene glycol:water), the composition applied to the burn-injured mammalian skin under conditions to ameliorate at least one consequence of the burn injury, the at least one consequence selected from the group consisting of partial-thickness deepithelialization, full-thickness necrosis, erythema, edema, eschar formation, blistering, and/or pain.

* * * * *